US007294758B2

(12) United States Patent
Polston et al.

(10) Patent No.: US 7,294,758 B2
(45) Date of Patent: Nov. 13, 2007

(54) MATERIALS AND METHODS FOR PRODUCING GEMINIVIRUS RESISTANT PLANTS

(75) Inventors: Jane E. Polston, North Port, FL (US); Ernest Hiebert, Gainesville, FL (US); Ahmed M. Abouzid, Gainesville, FL (US); Wayne B. Hunter, Orlando, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 174 days.

(21) Appl. No.: 11/134,994

(22) Filed: May 23, 2005

(65) Prior Publication Data

US 2005/0289671 A1    Dec. 29, 2005

Related U.S. Application Data

(63) Continuation of application No. 09/491,063, filed on Jan. 25, 2000, now abandoned.

(60) Provisional application No. 60/117,151, filed on Jan. 25, 1999.

(51) Int. Cl.
*C12N 15/33* (2006.01)
*C12N 15/63* (2006.01)
*C12N 15/82* (2006.01)
*A01H 5/10* (2006.01)
*A01H 5/00* (2006.01)

(52) U.S. Cl. .................. 800/280; 800/288; 800/293; 800/294; 800/317.3; 800/317.4; 435/469; 435/470; 435/411; 435/414; 435/419; 435/320.1; 536/23.1; 536/23.2; 536/23.72

(58) Field of Classification Search ...................... None
See application file for complete search history.

(56) References Cited

U.S. PATENT DOCUMENTS

| 5,194,596 A | 3/1993 | Tischer et al. |
| 5,350,836 A | 9/1994 | Kopchick et al. |
| 6,291,743 B2 | 9/2001 | Stout et al. |

FOREIGN PATENT DOCUMENTS

| WO | WO97/07217 | 2/1997 |
| WO | WO97/39110 | 10/1997 |
| WO | WO97/42315 | 11/1997 |
| WO | WO98/04724 | 2/1998 |
| WO | WO98/44136 | 10/1998 |

OTHER PUBLICATIONS

Gilbertson et al 1993 J. Gen. Virol. 74:23-31.*
Abouzid, A.M. et al. "The nucleotide sequence of tomato mottle virus, a new geminivirus isolated from tomatoes in Florida" *J. Gen. Virology*, 1992, pp. 3225-3229, vol. 73.
Abouzid, A.M. et al. (1996) "Modified coat protein of tomato-mottle geminivirus confers resistance in transgenic tobacco" *Phytopathology*, 1996, p. 583, vol. 86, No. 11, Suppl. Abstract No. 832A.
Bendahmane, M. et al. "Engineering resistance against tomato yellow leaf curl virus (TYLCV) using antisense RNA" *Plant Molecular Biology*, 1997, pp. 351-357, vol. 33, No. 2.
Brown, J.K. et al. "First Report of an Epidemic in Tomato Caused by Two Whitefly-Transmitted Geminiviruses in Puerto Rico" *Plant Disease* 1995, p. 1250, vol. 79.
Brunetti, A. et al. "High Expression of Truncated Viral Rep Protein Confers Resistance to Tomato Yellow Leaf Curl Virus in Transgenic Tomato Plants" *Mol. Plant-Microbe Interact.*, 1997, pp. 571-579, vol. 10, No. 5.
Cahill, M. et al. "Baseline determination and detection of resistance to imidacloprid in *Bemisia tabaci* (Homoptera: Aleyrodidae)" *Bull. of Ento. Res.*, 1996, pp. 343-349, vol. 86.
Career, H. et al. "Targeted Insertion of Foreign Genes into the Tobacco Plastid Genome without Physical Linkage to the Selectable Marker Gene" *Bio/Technology*, 1995, pp. 791-794, vol. 13.
Duan, Y.-P. et al. "Molecular Characterization of the Nonstructural Protein Genes of Tomato Mottle Virus and Development of Transgenic Plants Resistant to the Virus (Geminivirus)" *Dissertation Abstracts International*, 1996, p. 3398, vol. 58, No. 7b.
Duan, Y.-P. et al. "Geminivirus Resistance in Transgenic Tobacco Expressing Mutated BC1 Protein" *Mol. Plant-Microbe Interact.*, 1997, pp. 1-5, vol. 10.
Duan, Y.-P. et al. "Phenotypic Variation in Transgenic Tobacco Expressing Mutated Geminivirus Movement/Pathogenicity (BC1) Proteins" *Mol. Plant-Microbe Interact.*, 1997, pp. 1065-1074, vol. 10, No. 9.
Hanson, S.F. et al. "Mutational Analysis of a Putative NTP-Binding Domain in the Replication-Associated Protein (AC1) of Bean Golden Mosaic Geminivirus" *Virology*, 1995, pp. 1-9, vol. 211.
Hong, Y. et al. "Virus Resistance in *Nicotiana benthamiana* Conferred by African Cassava Mosaic Virus Replication-Associated Protein (AC1) Transgene" *Mol. Plant-Microbe Interact.*, 1996, pp. 219-225, vol. 9, No. 4.
Noris, E. et al. "Resistance to Tomato Yellow Leaf Curl Geminivirus in *Nicotiana benthamiana* Plants Transformed with a Truncated Viral C1 Gene" *Virology*, 1996, pp. 130-138, vol. 224.

(Continued)

*Primary Examiner*—Russell P. Kallis
*Assistant Examiner*—Brent T Page
(74) *Attorney, Agent, or Firm*—Saliwanchik, Lloyd & Saliwanchik

(57) ABSTRACT

The subject invention pertains to materials and methods for producing plants that are resistant to infection by geminiviruses and other related viruses. Methods of the invention comprise transforming a plant with a polynucleotide wherein when the polynucleotide is expressed in the plant, the transformed plant exhibits resistance to plant viral infections. Exemplified herein is the use of a polynucleotide encoding a Rep protein derived from tomato mottle geminivirus. The methods of the invention can be used to provide resistance to viral infection in plants such as tomato and tobacco. The present invention also concerns transformed and transgenic plants in plant tissue that express a polynucleotide encoding a plant virus Rep protein, or a fragment or variant thereof.

16 Claims, 3 Drawing Sheets

OTHER PUBLICATIONS

Polston, J.E. et al. "Spatial and Temporal Dynamics of Tomato Mottle Geminivirus and *Bemisia tabaci* (Genn.) in Florida Tomato Fields" *Plant Disease*, 1996, pp. 1022-1028, vol. 80, No. 9.

Polston, J.E. et al. "The Emergence of Whitefly-Transmitted Geminiviruses in Tomato in the Western Hemisphere" *Plant Disease*, 1997, pp. 1358-1369, vol. 81, No. 12.

Polston, J.E. et al. "Introduction of Tomato Yellow Leaf Curl Virus in Florida and Implications for the Spread of This and Other Geminiviruses of Tomato" *Plant Disease*, 1999, pp. 984-988, vol. 83, No. 11.

Sinisterra, X.H. et al. "RNA-mediated virus resistance in tobacco plants transformed with a modified coat protein of tomato mottle geminivirus?" *Phytopathology*, 1997, p. S91, vol. 87, No. 6.

Sinisterra, X.H. et al. "Tobacco Plants Transformed with a Modified Coat Protein of Tomato Mottle Begomovirus Show Resistance to Virus Infection" *Phytopathology*, 1999, pp. 701-706, vol. 89, No. 8.

Stout, J.T. et al. "Engineered rep Gene-Mediated Resistance to Tomato Mottle Geminivirus in Tomato" *Phytopathology*, 1997, p. S94, vol. 87.

Williams, L. et al. "Whitefly Control in Arizona: Development of a Resistance Management Program for Imidacloprid" Cotton Insect Research and Control Conference, 1996 Beltwide Cotton Conferences, pp. 752-755.

Pilbeam, C.C. et al. "Comparison of the Effects of Various Lengths of Synthetic Human Parathyroid Hormone-Related Peptide (hPTHrP) of Malignancy on Bone Resorption and Formation in Organ Culture" *Bone*, 1993, pp. 717-720, vol. 14.

Vukicevic, S. et al. Induction of nephrogenic mesenchyme by osteogenic protein 1 (bone morphogenetic protein 7) *Proc. Natl. Acad. Sci. USA*, 1996, pp. 9021-9026, vol. 93.

Benjamin, L. et al. "A plasticity window for blood vessel remodelling is defined by pericyte coverage of the preformed endothelial network and is regulated by PDGF-B and VEGF" *Development*, 1998, pp. 1591-1598, vol. 125.

Doerks, T. et al. "Genetwork, Protein annotation: detective work for function prediction" *TIG*, Jun. 1998, pp. 248-250, vol. 14, No. 6.

Bork, P. et al. "Genetwork, Go hunting in sequence databases but watch out for the traps" *TIG*, Oct. 1996, pp. 248-250, vol. 12, No. 10.

Smith, T. F. et al. The challenges of genome sequence annotation or "The devil is in the details" *Nature Biotechnology*, Nov. 1997, pp. 1222-1223, vol. 15.

Brenner, S. E. et al. "Errors in genome annotation" *TIG*, Apr. 1999, pp. 132-133, vol. 15, No. 4.

Skolnick, J. et al. "From genes to protein structure and function: novel applications of computational approaches in the genomic era" *Trends in Biotech*, 2000, pp. 34-39, vol. 18, No. 1.

Bork, P. "Powers and Pitfalls in Sequence Analysis: The 70% Hurdle" *Genome Research*, 2000, pp. 398-400.

Ngo, J. T. et al. "Computational Complexity, Protein Structure Prediction, and the Levinthal Paradox" In *The Protein Folding Problem and Tertiary Structure Prediction*, 1994, pp. 491-495, eds. K. Merz, Jr. et al., Birkhauser Boston.

Wells, J. A. "Additivity of Mutational Effects in Proteins" *Biochemistry*, Sep. 18, 1990, pp. 8509-8517, vol. 29, No. 37.

* cited by examiner

SEQUENCE LISTING

<160> NUMBER OF SEQ ID NOS: 2

<210> SEQ ID NO 1
<211> LENGTH: 1083
<212> TYPE: DNA
<213> ORGANISM: Tomato mottle geminivirus

<400> SEQUENCE: 1

```
atgcccccac caaagaaatt tagagttcag tcaaagaact atttcctaac ttatccccag      60
tgctctctat ctaaagaaga agcactttcc caattacaaa acctaaatac cccagtcaac     120
aagaaattca tcaaaatttg cagagagctt catgaaaatg gggaacctca tctccatgtg     180
cttgttcagt tcgaaggtaa gtaccaatgc acgaataaca gattcttcga cctggtctcc     240
ccaacccggt cagcacattt ccatccgaat attcagggag ctaaatcgag ctccgacgtc     300
aaatcataca tcgacaagga cggagataca atcgaatggg gagatttcca aatcgacggc     360
agatctgcca gaggaggcca gcagtctgct aatgattcat atgcgaaagc attaaatgca     420
ggttcggttc aatctgcctt agcggttcta agggaagaac aaccaaaaga ttttgtatta     480
caaaatcata acatccgctc taacctagaa cgaatattcg caaggctccc ggaaccgtgg     540
gttcctccat ttcaagtctc ttctttcact aacgttcctg acgagatgca ggaatgggcg     600
gataattatt tcgggacggg tgacgctgcg ccgccggata gacctgtaag tatcatcgtc     660
gagggtgatt caagaacagg gaagacgatg tgggcgcgtg cgttaggccc acataactat     720
ctcagtggac acctagactt caatggtcga gtcttctcga atgatgtgca gtataacgtc     780
attgatgaca tcgcaccgca ttatctaaag ctaaagcact ggaaagaatt gctgggggcc     840
cagaaagatt ggcaatcaaa ttgcaagtac ggtaagccag ttcaaattaa aggcggaatc     900
ccagcaatcg tgctttgcaa tcctggtgag ggtgccagct ataaagagtt cttagacaaa     960
gcagaaaata caggtctcaa gaactggact atcaagaatg cgatcttcat caccctcaca    1020
gccccctct atcaagagag cacacaggca agccaagaaa cgggcaatca gaaggcgcag    1080
ggt                                                                 1083
```

<210> SEQ ID NO 2
<211> LENGTH: 361
<212> TYPE: PRT
<213> ORGANISM: Tomato mottle geminivirus

<400> SEQUENCE: 2

```
Met Pro Pro Pro Lys Lys Phe Arg Val Gln Ser Lys Asn Tyr Phe Leu
1               5                   10                  15

Thr Tyr Pro Gln Cys Ser Leu Ser Lys Glu Glu Ala Leu Ser Gln Leu
            20                  25                  30

Gln Asn Leu Asn Thr Pro Val Asn Lys Lys Phe Ile Lys Ile Cys Arg
        35                  40                  45

Glu Leu His Glu Asn Gly Glu Pro His Leu His Val Leu Val Gln Phe
    50                  55                  60

Glu Gly Lys Tyr Gln Cys Thr Asn Asn Arg Phe Phe Asp Leu Val Ser
65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Thr Ile Glu
            100                 105                 110
```

-continued

```
Trp Gly Asp Phe Gln Ile Asp Gly Arg Ser Ala Arg Gly Gly Gln Gln
        115                 120                 125

Ser Ala Asn Asp Ser Tyr Ala Lys Ala Leu Asn Ala Gly Ser Val Gln
        130                 135                 140

Ser Ala Leu Ala Val Leu Arg Glu Glu Gln Pro Lys Asp Phe Val Leu
145                 150                 155                 160

Gln Asn His Asn Ile Arg Ser Asn Leu Glu Arg Ile Phe Ala Lys Ala
                165                 170                 175

Pro Glu Pro Trp Val Pro Pro Phe Gln Val Ser Ser Phe Thr Asn Val
                180                 185                 190

Pro Asp Glu Met Gln Glu Trp Ala Asp Asn Tyr Phe Gly Thr Gly Asp
        195                 200                 205

Ala Ala Pro Pro Asp Arg Pro Val Ser Ile Ile Val Glu Gly Asp Ser
        210                 215                 220

Arg Thr Gly Lys Thr Met Trp Ala Arg Ala Leu Gly Pro His Asn Tyr
225                 230                 235                 240

Leu Ser Gly His Leu Asp Phe Asn Gly Arg Val Phe Ser Asn Asp Val
                245                 250                 255

Gln Tyr Asn Val Ile Asp Asp Ile Ala Pro His Tyr Leu Lys Leu Lys
                260                 265                 270

His Trp Lys Glu Leu Leu Gly Ala Gln Lys Asp Trp Gln Ser Asn Cys
        275                 280                 285

Lys Tyr Gly Lys Pro Val Gln Ile Lys Gly Gly Ile Pro Ala Ile Val
        290                 295                 300

Leu Cys Asn Pro Gly Glu Gly Ala Ser Tyr Lys Glu Phe Leu Asp Lys
305                 310                 315                 320

Ala Glu Asn Thr Gly Leu Lys Asn Trp Thr Ile Lys Asn Ala Ile Phe
                325                 330                 335

Ile Thr Leu Thr Ala Pro Leu Tyr Gln Glu Ser Thr Gln Ala Ser Gln
                340                 345                 350

Glu Thr Gly Asn Gln Lys Ala Gln Gly
        355                 360
```

MATERIALS AND METHODS FOR PRODUCING GEMINIVIRUS RESISTANT PLANTS

CROSS-REFERENCE TO RELATED APPLICATIONS

This application is a continuation of U.S. application Ser. No. 09/491,063, filed Jan. 25, 2000 now abandoned, which claims the benefit of U.S. Provisional Application No. 60/117,151, filed Jan. 25, 1999.

The subject invention was made with government support under a research project supported by USDA Grant No. 92341357456 and USDA Grant No. 98341356784. The government has certain rights in this invention.

BACKGROUND OF THE INVENTION

Whitefly-transmitted geminiviruses have become a major limiting factor in tomato production in Florida, the Caribbean and much of Latin America. This group of viruses is currently expanding in the Western Hemisphere, and the number of characterized geminiviruses which infect tomato in this region has increased from three to more than 17 over the last 10 years (Polston and Anderson, 1997). This expansion is continuing and reports of new epidemics are appearing almost monthly. Whitefly-transmitted viruses appear alone and in mixed infections with other geminiviruses and other viruses. Whitefly-transmitted geminiviruses are reducing tomato yields in many countries, and total crop losses are not uncommon (Polston and Anderson, 1997). Tomato production in Florida has suffered significant losses (estimated at $125 million in 1990-91) due to tomato mottle virus (ToMoV) infection, which first appeared in 1989. There are no estimates of losses in Puerto Rico due to the tomato geminiviruses, potato yellow mosaic virus (PYMV) and ToMoV, but yields have been reduced significantly (Brown et al., 1995). Tomato yellow leaf curl virus (TYLCV-Is) which caused extensive losses to tomato production in the Dominican Republic (reviewed by Polston and Anderson, 1997) has now been found in Florida (Polston et al., 1999). Incidences of TYLCV-Is are increasing and economic losses were felt this past fall (1998). TYLCV-Is is widespread in Florida, is likely to increase over the next few years and will become a major constraint to tomato production in Florida.

Geminiviruses are very difficult to economically manage in fresh market tomatoes, and practically impossible to manage in processing tomatoes. At this time geminiviruses are managed primarily through the use of a single insecticide, imidacloprid, to reduce the population of the whitefly vector. Tolerance to this insecticide has already been reported from other countries (Cahill et al., 1996; Williams et al., 1996). It may be only a matter of time before imidacloprid loses efficacy in the United States and other locations. The average Florida tomato grower spent approximately $250/acre for insecticides to control ToMoV in 1994 through 1997. These costs are expected to increase significantly as growers' struggle to manage TYLCV-Is. In Caribbean countries geminiviruses have caused many small and medium size tomato growers to go out of business due the increases in costs of production and crop losses. In Israel, where imidacloprid resistance is present, TYLCV-Is is managed by pesticide use plus exclusion; tomatoes are produced in greenhouses enclosed in whitefly-proof screening material or in screened tunnels in the field. The use of these methods are expensive and are often not an economically or horticulturally realistic alternative. The least expensive and most practical control of whitefly-transmitted geminiviruses is the use of resistant cultivars. At this time there are no commercially available resistant tomato cultivars for the geminiviruses native to the Western Hemisphere. There are several cultivars available which have tolerance to TYLCV-Is, however the fruit size and the horticultural attributes of these cultivars are unsuitable for production in Florida.

There are no commercially available ToMoV-resistant tomato cultivars. ToMoV-resistance from *Lycopersicon* species has been incorporated into tomato (*L. esculentum*) backgrounds but resistance is closely linked with small fruit size. This linkage has significantly delayed development of resistant plants. Resistance to ToMoV in both tobacco and tomato has been described using mutated coat protein and movement protein genes from ToMoV (Abouzid et al., 1996; Duan et al., 1997a; Duan et al., 1997b; Polston et al., 1996; Sinisterra et al., 1997; Sinisterra et al., 1999). A mutated BC1 gene has been shown to give broad-spectrum resistance (Duan et al., 1997a).

There are few reports suggesting that the gene encoding the geminivirus replication associated protein (Rep) might be used for resistance. There has been a report that a modified ToMoV Rep mutated in a NTP-binding motif was transformed into tomato plants and demonstrated to interfere with viral replication (Stout et al., 1997). Hanson et al. (1995) analyzed phenotypes of BGMV (bean golden mosaic virus) with mutations in a NTP-binding motif of the Rep gene, and demonstrated that the NTP-binding domain is required for replication. They proposed that mutations in this motif may serve in a trans-dominant negative interference scheme for pathogen-derived resistance (also known as "dominant negative mutations"). Resistance to African cassava mosaic geminivirus (ACMV) in *Nicotiana benthamiana* plants was developed by transformation with ACMV Rep (Hong and Stanley, 1996).

Resistance has been reported with the Rep gene of a monopartite virus, tomato yellow leaf curl virus (TYLCV), a geminivirus only distantly related to ToMoV. Noris et al. (1996) found TYLCV-resistance in *N. benthamiana* plants using the TYLCV Cl gene with a truncated C-terminal (210 amino acids). However, resistance was overcome with time. Brunetti et al. (1997) transformed tomatoes with the same construct and found that high accumulation of the truncated Rep protein was required for resistance, that high accumulation resulted in a "curled" phenotype, and that the resistance did not extend to an unrelated geminivirus. The plants transformed according to the methods of the subject invention have a normal phenotype and are high yielding as well.

BRIEF SUMMARY OF THE INVENTION

The subject invention pertains to materials and methods for producing plants that are resistant to infection by geminiviruses and other related viruses. Methods of the invention comprise transforming a plant with a polynucleotide wherein when the polynucleotide is expressed in the plant, the transformed plant exhibits resistance to infection when challenged with a plant virus. In a preferred embodiment, a plant is transformed with a polynucleotide encoding a Rep protein or a mutated Rep protein derived from tomato mottle geminivirus or from tomato yellow leaf curl virus (TYLCV-Is). The methods of the invention can be used to provide resistance to viral infection in plants such as tomato and tobacco.

The subject invention also concerns polynucleotides that encode the Rep protein and mutated Rep proteins of the invention. The mutated Rep proteins are also an object of the present invention.

The present invention also concerns transformed and transgenic plants and plant tissue that contain or express a polynucleotide encoding a Rep protein or a mutated Rep protein.

BRIEF DESCRIPTION OF THE DRAWINGS

FIG. 1A shows disease progress curves of ToMoV in 'Agriset 761' and 6 tomato lines transformed with ToMoV Rep gene. FIG. 1B shows the mean number of immature whiteflies per ten terminal leaflets.

FIG. 2A shows disease progress curves of ToMoV in 'Agriset 761', FL 7324, FL 7613 and 4 tomato lines transformed with ToMoV Rep gene. FIG. 2B shows the mean number of immature whiteflies per ten terminal leaflets.

FIG. 3A shows disease progress curves of ToMoV in 'Agriset 761', FL 7324, FL 7613, and 5 tomato lines transformed with ToMoV Rep gene. FIG. 3B shows the mean number of immature whiteflies per ten terminal leaflets.

BRIEF DESCRIPTION OF THE SEQUENCES

Figure 1A:
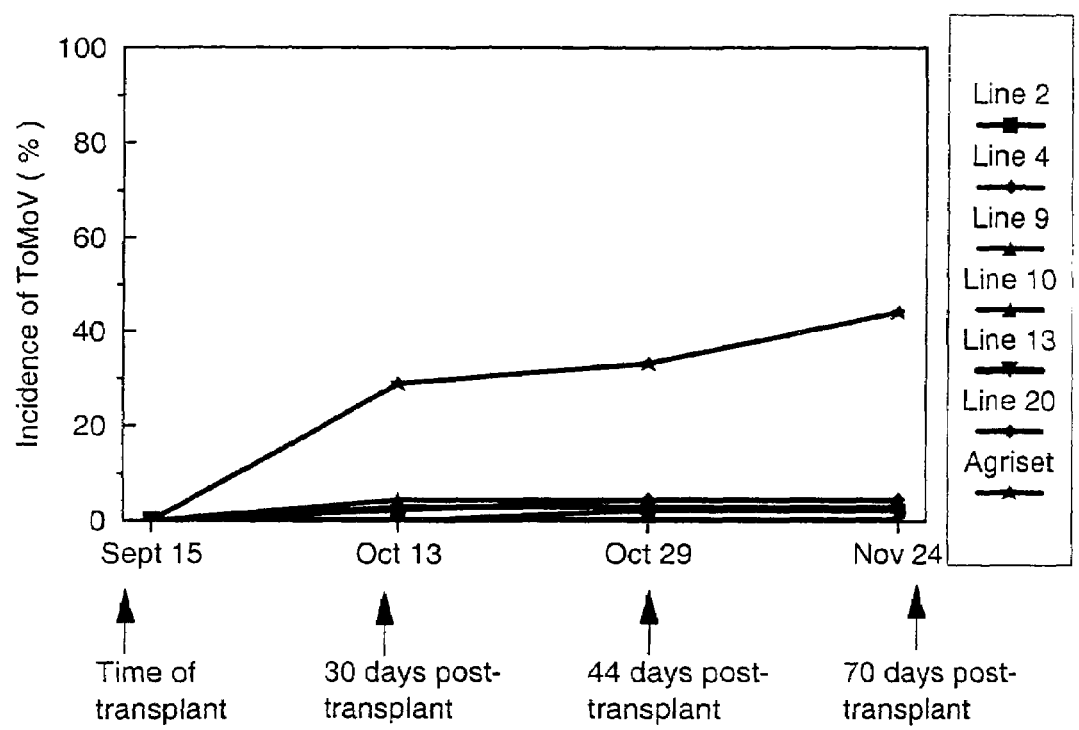
FIGS. 1A and 1B show a Field Resistance Trial conducted in Fall 1997.

SEQ ID NO: 1 shows the nucleotide sequence of the protein coding region of the Rep gene of tomato mottle geminivirus.

SEQ ID NO: 2 shows the amino acid sequence of the Rep protein encoded by the nucleotide sequence of SEQ ID NO: 1.

DETAILED DESCRIPTION OF THE INVENTION

The subject invention concerns the use of a plant virus gene to transform a plant or plant tissue to confer resistance in the plant or plant tissue to infection from a plant virus. The methods of the subject invention can be used to confer resistance in a plant to infection by a plant pathogen such as, for example, a geminivirus. The method comprises transforming a plant with a polynucleotide such that when the polynucleotide is expressed in the plant the plant then exhibits resistance to infection by plant viruses. In one embodiment of the invention, a plant is transformed by wounding and agroinfection with an *Agrobacterium* containing a polynucleotide of the invention that is transferred to the plant upon agroinfection of the plant. Preferably, the polynucleotide used in the methods of the invention encodes a plant virus Rep protein or a mutant Rep protein, or a fragment or variant thereof. In an exemplified embodiment, the polynucleotide encodes a Rep protein of tomato mottle geminivirus (ToMoV) (SEQ ID NO: 2). The nucleotide sequence of a ToMoV (component A) virus is disclosed in Genbank having accession number L14460. Abouzid et al. (1992) disclose the nucleotide sequence of the ToMoV Rep gene (referred to therein as AL1 and corresponding to nucleotides 1523 to 7 of the sequence shown in FIG. 1 of Abouzid et al. (1992) (SEQ ID NO: 1)). In another embodiment, the polynucleotide encodes a tomato yellow leaf curl virus (TYLCV-Is) Rep protein. The nucleotide sequences of several TYLCV-Is viral isolates are disclosed in Genbank, including isolates from Israel (accession number X15656), Cuba (accession number AJ223505), Dominican Republic (accession number AF024715), Egypt (accession number L12219), Jamaica (accession number U84146), Lebanon (accession number AF160875), Mexico (accession number AF168709) and Spain (accession number AJ223505).

In a preferred embodiment of the invention, a virus-resistant transgenic plant line prepared according to the methods described herein is crossed with a transgenic plant line that is resistant to the same virus and derived from a different transformation event to produce hybrids that exhibit increased virus resistance over the parent lines.

The methods of the subject invention can be used to confer resistance in plants to infection by viruses such as geminiviruses, and include, for example, tomato mottle virus, cabbage leaf curl geminivirus, potato yellow mosaic virus, tomato golden mosaic virus, tomato yellow mosaic virus, tomato leaf crumple virus, tomato yellow leaf curl virus, pepper huasteco virus and others. Plants which can be transformed according to the methods of the subject invention include, but are not limited to, tomato and tobacco.

The subject invention also concerns polynucleotide molecules that encode modified or mutated forms of a plant virus Rep protein which when expressed in a plant confers resistance to infection by plant viruses. In one embodiment, the polynucleotide encodes a Rep protein of ToMoV or TYLCV-Is. Modifications and mutations contemplated within the scope of the invention include Rep proteins comprising amino acid substitutions, deletions, and insertions. Also contemplated within the scope of the invention are Rep polypeptides containing the mutations in the amino acid sequence.

The subject invention also concerns recombinant polynucleotide molecules comprising a vector in which a polynucleotide sequence encoding a plant virus Rep protein, or a mutant thereof, which is expressible in a suitable host plant has been inserted. Suitable vectors may be selected from those known in the art including plasmids, phage DNA, or derivatives or fragments thereof, or combinations of plasmids and phage DNA, and yeast plasmids. The polynucleotide encoding the Rep protein can be inserted into the multiple cloning site of a vector, such as the commercially available pUC vectors or the pGEM vectors, which allow for the excision of the polynucleotide having restriction termini adapted for insertion into any desirable plant expression or integration vector. In addition, regulatory sequences such as promoters can be operatively linked to the coding sequences of the polynucleotides of the present invention. For example, the 35S promoter of cauliflower mosaic viruses (CaMV) can be used with the subject invention. Other plant expression vectors can also be used in the present invention.

The present invention also concerns cells infected, transformed, or transfected with a polynucleotide of the present invention that encodes a Rep protein or a mutated Rep protein. Preferably, the Rep protein or mutant thereof is derived from ToMoV or TYLCV-Is. In one embodiment, the polynucleotide is inserted into a suitable vector, and the recombinant vector is used to transform a bacterium or other host which can then be used to introduce the polynucleotide into a plant cell. Suitable hosts that can be infected, transformed, or transfected with the polynucleotide of the invention include gram positive and gram negative bacteria such as *E. coli* and *Bacillus subtilis*. Other suitable hosts include *Agrobacterium* cells, insect cells, plant cells, and yeast cells. *Agrobacterium* containing the polynucleotide of the invention can be used to transform plant cells with the polynucleotide according to standard methods known in the art. Polynucleotides can also be introduced into plant cells by a biolistic method (Carrer, 1995) and other methods known in the art.

The subject invention also concerns transformed and transgenic plants and plant tissue, including plant seeds, that exhibit resistance to infection by plant geminiviruses such as ToMoV and the like. In one embodiment, a transformed or transgenic plant of the invention comprises a polynucleotide that encodes a Rep protein or a mutated Rep protein. Preferably, the Rep protein or mutated Rep protein is derived from ToMoV or TYLCV-Is. Transformed and transgenic plants and plant tissue of the invention can be prepared from plants such as tomato, tobacco and others.

As those of ordinary skill in the art will appreciate, any number of different nucleotide sequences can be used, based on the degeneracy of the genetic code, to encode a Rep protein or a mutated Rep protein of the present invention. Accordingly, any polynucleotide sequence which encodes a Rep protein or mutated Rep protein, or a fragment or variant thereof, falls within the scope of this invention.

Two hybrid parent tomato lines (from J. W. Scott) FL 7324 and FL 7613, were transformed with the ToMoV Rep gene in the sense orientation. Both tolerance and immunity to ToMoV were seen in plants containing the transgene in $T_1$ through $T_4$ generations. Preliminary Southern analysis has indicated that resistant plants have either one or two genes. Resistance has been evaluated in the field in the fall and spring seasons of 1996, 1997, and 1998. Plants in the field were selected for resistance and horticultural qualities. Yields of transformed plants were equivalent to non-transformed plants in the absence of virus, and were significantly greater in the presence of ToMoV. Transformed plants appeared to have high levels of tolerance to ToMoV.

Resistance to infection was evaluated by simulating natural inoculation as much as possible. Other laboratories use such techniques as biolistic and Agro-inoculation, which never occur naturally, and bypass the normal modes of entry into the plant cell where resistance mechanisms may exist. The inoculation described herein is a simulation of a worst case scenario in a transplant house or a grower's field. Plants are inoculated at an early stage in development, when plants are highly attractive to whiteflies and are highly susceptible to infection by ToMoV. Whiteflies are reared on virus-infected tomato plants, which eliminates the interference of whitefly feeding preferences, and is similar to inoculation by viruliferous whiteflies in the field (Polston et al., 1996). This inoculation protocol results in an inoculation efficiency of 100%.

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Field Evaluation of Transgenic Resistance to ToMoV

Advanced breeding lines, FL 7324 and FL 7613 were transformed with ToMoV Rep gene using standard *Agrobacterium*-mediated transformation techniques. A vector comprising a 35S CaMV (non-enhanced) promoter linked to the Rep gene was used in the transformation. Plant tissue was wounded using tungsten. Plants that contained a Rep transgene were identified using PCR methods. Those plants were then evaluated for resistance to viral infection. Untransformed parents and transformed lines from three different transformation events were evaluated for resistance to ToMoV and for yield, both in the presence and absence of ToMoV. Lines shown in the following tables are four generations past transformation. Lines 02 and 04 are from the same $T_0$ plant in a FL 7613 background, lines 09 and 10 are from a second $T_0$ plant and their background is FL 7324, and lines 11 and 12 are from a third $T_0$ plant, and their background is FL 7613.

Southern analysis using two restriction enzymes, one which cut inside the transgene and one which cut outside the transgene, of several lines of Rep-transformed tomatoes revealed that the ToMoV resistance in 4 of the R4 generation lines (lines 02, 04, 11, 12) appeared to be due to one insertion site and one copy of the transgene. Multiple copies were present in resistant lines 09 and 10. Lines 02 and 04, 11 and 12, and 09 and 10 were the result of three different transformations.

EXAMPLE 2

Performance in the Presence of ToMoV and Whiteflies

For three seasons, Fall 1997, Spring 1998, and Fall 1998, tomato transplants to be evaluated were set into a field which was within 20 feet of a large block of tomatoes which was a continuous source of viruliferous whiteflies throughout the season. No imidacloprid was applied to the plants being evaluated but attempts were made to keep whitefly populations below a threshold which would result in irregular ripening of the fruit (20 immature whitefly/10 terminal leaflets). Whitefly populations were evaluated approximately every 2 week beginning about 4 week after transplanting. Whitefly populations varied each season, with the highest populations occurring in the Fall 1998 trial. The trials consisted of 15 plants per block, with three replications, in a randomized complete block design. Plants were evaluated every other week for the presence of whiteflies and virus. Plants displaying virus-like symptoms were assayed by nucleic acid hybridization to confirm the presence of ToMoV. Fruit were harvested from plants in two pickings, graded, and marketable yields were calculated.

EXAMPLE 3

Yields

Results are shown in Tables 1, 2 and 3. The transformed lines yielded as much or more than the untransformed parents and the commercial hybrid 'Agriset' in all three trials. The best transformed lines, 02, 04, 11 and 12 yielded approximately 50%-100% more marketable fruit than the untransformed lines. Yields of these transformed lines in the presence of ToMoV and whiteflies were comparable to yields of the untransformed lines in the absence of virus and whiteflies. In addition, transformed plants yielded well in both fall and spring production seasons.

EXAMPLE 4

ToMoV Resistance

Figure 1B:
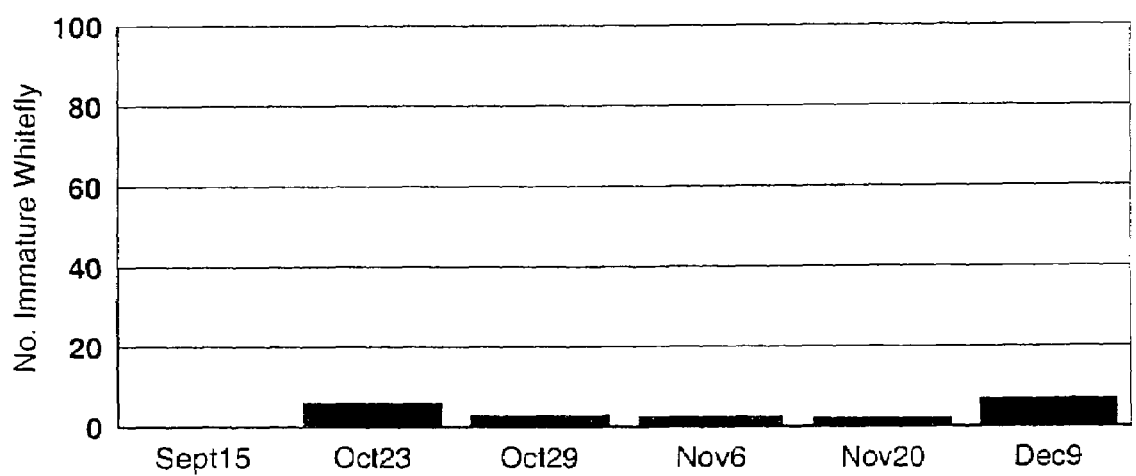
Figure 2A:
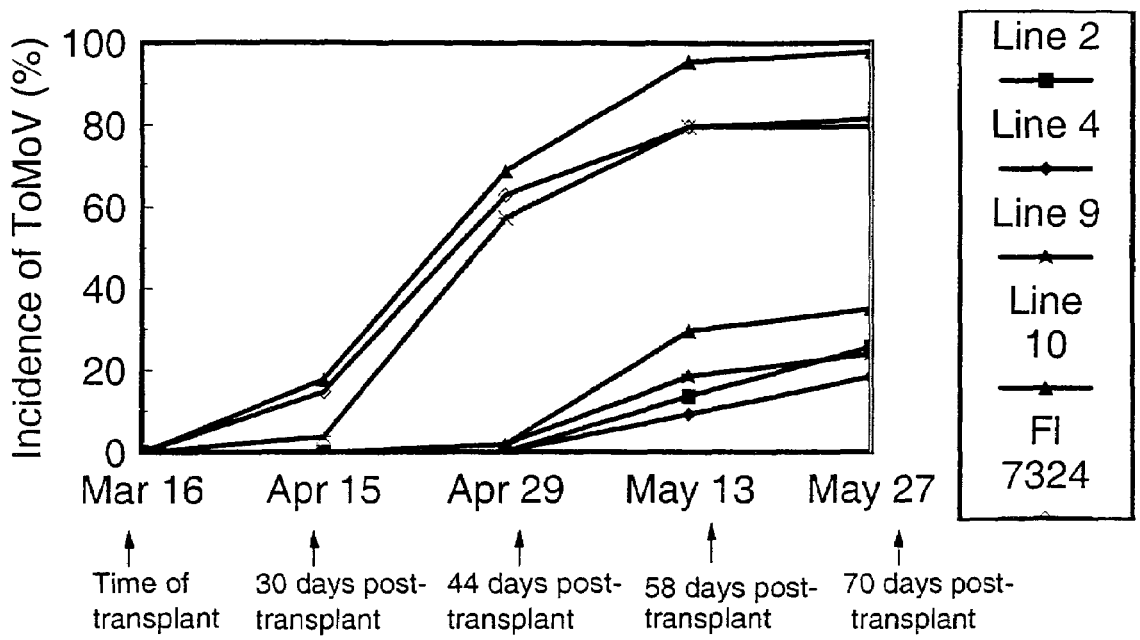
FIGS. 2A and 2B show a Field Resistance Trial conducted in Spring, 1998.
Figure 2B:
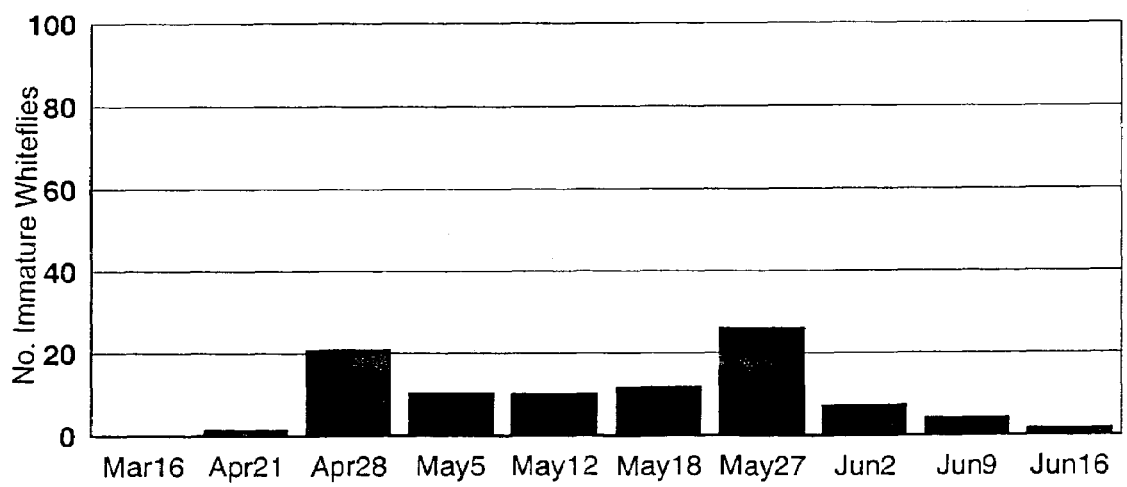
Figure 3A:
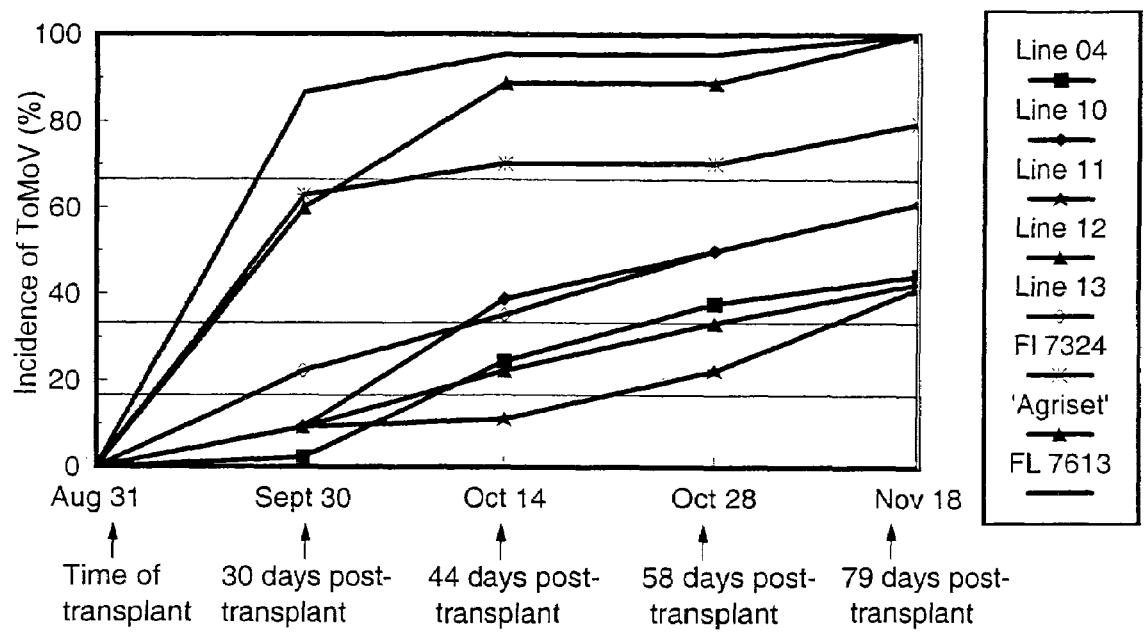
FIGS. 3A and 3B show a Field Resistance Trial conducted in Fall 1998.
Figure 3B:
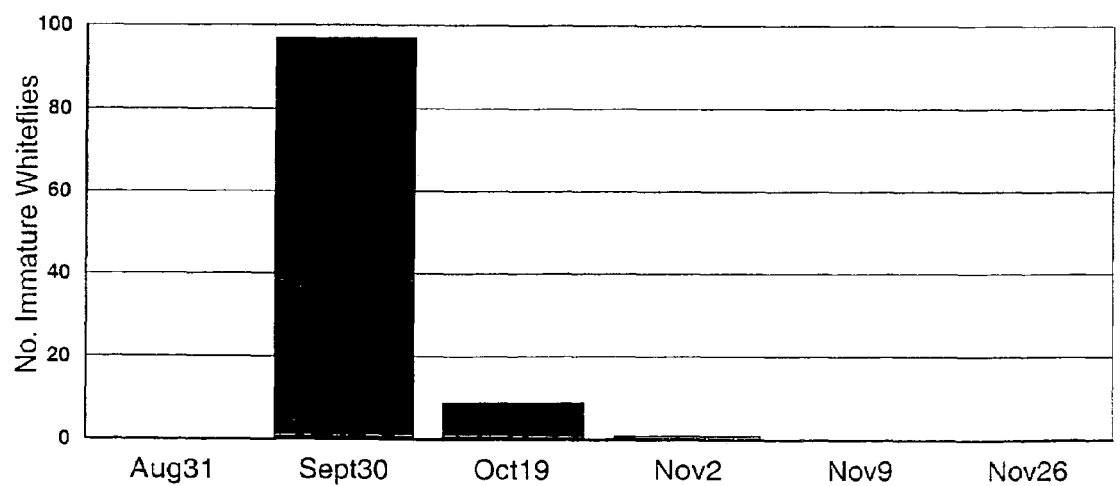

Infection rates as determined by viral nucleic acid detection, were much lower in all transformed lines than in untransformed lines. Transformed lines have high levels of tolerance, which were overcome only with high populations of viruliferous whiteflies. FIGS. 1A, 2A, and 3A show the disease progress curves from untransformed and transformed lines from trials over three seasons. The highest rates of infection were observed in the Fall 1998 season (FIGS. 3A and 3B) which had extremely high populations of viruliferous whiteflies (at 100 per 10 terminal leaflets).

Even with those unusually high populations, transformed lines though infected produced yields similar to those plants not exposed to virus (Tables 3 and 6). Symptoms in infected transformed plants were milder than those of infected untransformed plants.

EXAMPLE 5

Performance in the Absence of ToMoV and Whiteflies

For three seasons, Fall 1997, Spring 1998, and Fall 1998, tomato transplants to be evaluated were set into a field which was not located near a source of ToMoV or whiteflies. Imidacloprid was applied at the time of transplant to the field, and plants were monitored weekly for whiteflies. When whiteflies were detected (about the 6 to 8 week after transplant) plants were sprayed with a rotation of insecticides to manage whitefly populations. This resulted in less than 0.1% infection of ToMoV in these plants, and allowed an evaluation of yields without the influence of virus. The trials consisted of 15 plants per block, with three replications, in a randomized complete block design. Plants displaying virus-like symptoms were assayed by nucleic acid hybridization to confirm the presence of ToMoV. Fruit were harvested from plants in two pickings, graded, and marketable yields were calculated.

EXAMPLE 6

Yield

Marketable yields of untransformed and transformed plants are shown in Tables 4, 5, and 6. Yields of transformed lines were either significantly greater (Table 4) or not significantly different to those of the transformed plants. The best yielding transformed lines were 02, 04, 11 and 12 which yielded as good or better than their untransformed parent, FL 7613 in the absence of ToMoV infection.

EXAMPLE 7

Hybrid Transgenic Tomatoes

Hybrid tomatoes were made by crossing transgenic lines with the untransformed genotype and between transgenic lines derived from different transformation events. It was found that several of the hybrids of different transgenic lines were more resistant to ToMoV than either open-pollinated parent. This is known as pyramiding of resistance genes and resulted in improved resistance of the transgenic plants to infection.

Transgenic lines 02 and 11 were crossed and their hybrid progeny was evaluated for yield and ToMoV resistance. An increase in resistance was observed in the hybrid. ToMoV resistance in the hybrids was superior to both the transformed parents and nontransformed parents (Table 7). Infection of the hybrid was 1/3 that of the transgenic parent and 1/10 that of the untransformed parent. Resistance appeared to be additive. Yields of these crosses are currently being analyzed but are expected to be high based on previous results with the untransformed parents. This data shows that hybridizing transgenic parents is a method to improve geminivirus resistance.

Tables 1-3 show a comparison of yields of ToMoV Rep-transformed tomatoes with untransformed parents and 'Agriset' in the presence of ToMoV and whiteflies.

Tables 4-6 show a comparison of yields of ToMoV Rep-transformed tomatoes with untransformed parents in the absence of ToMoV and whiteflies.

TABLE 1

Fall 1997 Trial

| Line | Total Marketable Yield (ca/A) | Extra Large Fruit (ca/A) | Avg. Fruit Size (lbs) | Culls (ca/A) |
|---|---|---|---|---|
| 02 | 1556.5 a | 766.7 a | 0.33 ab | 580.8 a |
| 04 | 1695.9 a | 952.5 a | 0.38 a | 580.8 a |
| 09 | 952.5 b | 92.9 c | 0.27 c | 511.1 a |
| 10 | 859.6 b | 69.7 c | 0.28 c | 464.6 a |
| FL 7324 | — | — | — | — |
| FL 7613 | — | — | — | — |
| Agriset | 952.5 b | 325.2 b | 0.31 bc | 325.2 b |

TABLE 2

Spring 1998 Trial

| Line | Total Marketable Yield (ca/A) | Extra Large Fruit (ca/A) | Avg. Fruit Size (lbs) | Culls (ca/A) |
|---|---|---|---|---|
| 02 | 1498.5 a | 1028.9 a | 0.394 a | 627.3 a |
| 04 | 1237.1 ab | 923.5 a | 0.373 a | 697.0 a |
| 09 | 1359.1 ab | 156.8 b | 0.266 bc | 592.4 a |
| 10 | 1341.6 ab | 174.2 b | 0.261 c | 609.8 a |
| FL 7324 | 906.1 ab | 139.4 b | 0.272 c | 592.4 a |
| FL 7613 | 784.1 b | 487.9 b | 0.365 a | 348.5 a |
| Agriset | 714.4 b | 278.8 b | 0.320 b | 331.1 a |

TABLE 3

Fall 1998 Trial

| Line | Total Marketable Yield (ca/A) | Extra Large Fruit (ca/A) | Avg. Fruit Size (lbs) | Culls[1] (ca/A) |
|---|---|---|---|---|
| 04 | 1702.9 a[2] | 1247.6 a | 0.377 a | 480.0 ab |
| 10 | 759.7 b | 30.2 b | 0.240 d | 736.5 a |
| 11 | 1689.0 a | 999.0 a | 0.358 ab | 573.8 ab |
| 12 | 1905.0 a | 1191.8 a | 0.356 ab | 573.8 ab |
| FL 7324 | 325.2 b | 23.2 b | 0.284 cd | 401.9 b |
| FL 7613 | 727.2 b | 464.6 b | 0.377 ab | 471.6 ab |
| Agriset | 580.8 b | 255.6 b | 0.323 bc | 325.3 b |

[1]Culls include all fruit rated not marketable (includes insect damage, disease, irregular shape, etc.)
[2]Letters after values denote significant differences as determined by Duncan's Multiple Range.

TABLE 4

Fall 1997 Trial

| Line | Total Marketable Yield (ca/A) | Extra Large Fruit (ca/A) | Avg. Fruit Size (lbs) | Culls (ca/A) |
|---|---|---|---|---|
| 02 | 1359.1 a | 731.8 a | 0.35 ab | 609.8 a |
| 04 | 1184.8 ab | 662.1 a | 0.35 ab | 592.4 a |
| 09 | 906.1 bc | 104.5 c | 0.27 c | 400.8 a |
| 10 | 609.8 cd | 22.7 c | 0.26 c | 435.6 ab |
| FL 7324 | 993.2 b | 278.8 bc | 0.32 b | 313.6 b |
| FL 7613 | 592.4 d | 435.6 ab | 0.37 a | 278.8 b |

TABLE 5

Spring 1998 Trial

| Line | Total Marketable Yield (ca/A) | Extra Large Fruit (ca/A) | Avg. Fruit Size (lbs) | Culls (ca/A) |
|---|---|---|---|---|
| 02 | 1968.9 a | 1219.7 ab | 0.36 b | 784.1 a |
| 04 | 2108.3 a | 1515.9 ab | 0.37 b | 784.1 a |
| 09 | 1986.3 a | 296.2 c | 0.29 c | 540.1 ab |
| 10 | 2265.1 a | 278.8 c | 0.26 d | 418.2 ab |
| FL 7324 | 2456.8 a | 906.0 bc | 0.30 a | 278.8 b |
| FL 7613 | 2317.4 a | 1812.1 a | 0.40 a | 435.6 ab |
| Agriset | 2352.2 a | 1550.7 ab | 0.36 b | 313.6 b |

TABLE 6

Fall 1998 Trial

| Line | Total Marketable Yield (ca/A) | Extra Large Fruit (ca/A) | Avg. Fruit Size (lbs) | Culls[1] (ca/A) |
|---|---|---|---|---|
| 02 | 1568.2 abc[2] | 911.3 b | 0.348 b | 412.9 a |
| 04 | 1503.7 abc | 1050.7 b | 0.368 b | 423.4 a |
| 09 | 744.0 d | 12.2 c | 0.240 d | 639.5 a |
| 10 | 998.4 cd | 64.5 c | 0.272 c | 557.6 a |
| 11 | 1747.6 ab | 1115.1 ab | 0.351 b | 597.6 a |
| 12 | 1742.4 ab | 1197.0 ab | 0.361 ab | 522.7 a |
| FL 7324 | 1184.8 bcd | 174.2 c | 0.270 c | 418.2 a |
| FL 7613 | 1951.5 a | 1510.7 a | 0.388 a | 418.2 a |
| Agriset | 1381.7 abcd | 876.4 d | 0.360 ab | 505.3 a |

[1]Culls include all fruit rated not marketable (includes insect damage, disease, irregular shape, etc.)
[2]Letters after values denote significant differences as determined by Duncan's Multiple Range.

TABLE 7

Evaluation of Resistance to ToMoV in a Hybrid of Two Transgenic Lines - Fall 1998 Trial

| Line | Transformation Status | Incidence of ToMoV (60 days post transp.)[1] |
|---|---|---|
| FL 7324 | not transformed | 100% |
| FL 7613 | not transformed | 100% |
| F97/02 | FL 7613- Rep | 36.7% |
| F97/11 | FL 7324 - Rep | 33.3% |
| $F_1$ | F97/0202 × F97/11 | 12% |

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Abouzid, A. M., J. E. Polston, and E. Hiebert (1992) "The nucleotide sequence of tomato mottle virus, a new geminivirus isolated from tomatoes in Florida" *J. Gen. Virology* 73:3225-3229.

Abouzid, A., J. E. Polston, W. B. Hunter, E. Hiebert (1996) "Modified coat protein of tomato mottle geminivirus confers resistance in transgenic tobacco" *Phytopathology* 86(11):593 Suppl. Abstract No. 832A.

Brown, J. K, J. Bird, G. Banks, M. Sosa, K. Kiesler, I. Cabrera, G. Fornaris (1995) "First report of epidemic in tomato caused by two whitefly-transmitted geminiviruses in Puerto Rico" *Plant Disease* 79:1250.

Brunetti, A., M. Tavazza, E. Noris, R. Tavazza, P. Caciagli, G. Ancora, S. Crespi, G. P. Accotto (1997) "High expression of truncated viral Rep protein confers resistance to tomato yellow leaf curl virus in transgenic tomato plants" *Mol. Plant-Microbe Interact.* 10:571-579.

Cahill, M., K. Gorman, S. Day, I. Denholm (1996) "Baseline determination and detection of resistance to imidacloprid in *Bemisia tabaci* (Homoptera:*Aleyrodidae*)" *Bull. of Ento. Res.* 86:343-349.

Carrer, H., P. Maliga (1995) "Targeted insertion of foreign genes into the tobacco plastid genome without physical linkage to the selectable marker gene" *Biotechnology* 13:791-794.

Duan, Y. -P., C. A. Powell, S. E. Webb, D. E. Purcifull, E. Hiebert (1997a) "Geminivirus resistance in transgenic tobacco expressing mutated BC1 protein" MPMI 10:1-5.

Duan, Y. -P., C. A. Powell, D. E. Purcifull, P. Broglio, E. Hiebert (1997b) "Phenotypic variation in transgenic tobacco expressing mutated geminivirus movement/pathogenicity (BC1) proteins" MPMI 10:1065-1074.

Hanson, S. F., R. A. Hoogstraten, P. Ahlquist, R. L. Gilbertson, D. R. Russell, D. P. Maxwell (1995) "Mutational analysis of a putative NTP-binding domain in the replication-associated protein (AC1) of bean golden mosaic geminivirus" *Virology* 211:1-9.

Hong, Y. and J. Stanley (1996) "Virus resistance in *Nicotiana benthamiana* conferred by African cassava mosaic virus replication-associated protein (AC1) transgene" *Mol. Plant-Microbe Interact.* 9:219-225.

Noris, E., G. P. Accotto, R. Tavazza, A. Brunetti, S. Crespi, M. Tavazza (1996) "Resistance to tomato yellow leaf curl geminivirus in *Nicotiano benthamiana* plants transformed with a truncated viral C1 gene" *Virology* 224:130-138.

Polston, J. E., D. O. Chellemi, D. J. Schuster, R. J. McGovern, P. A. Stansly (1996) "Spatial and tremporal dynamics of tomato mottle geminivirus and *Bemisia tabaci* in Florida tomato fields" *Plant Disease* 80:1022-1028.

Polston, J. E. and P. K. Anderson (1997) "The emergence of whitefly-transmitted geminiviruses in tomato in the Western hemisphere" *Plant Disease* 81:1358-1369.

Polston, J. E., R. J. McGovern, L. G. Brown (1999) "Introduction of tomato yellow leaf curl virus in Florida and implications for the spread of this and other geminiviruses of tomato" *Plant Dis.* 83:984-988.

Sinisterra, X., J. E. Polston, E. Hiebert, A. Abouzid (1997) "RNA-mediated virus resistance in tobacco plants transformed with a modified coat protein of tomato mottle geminivirus" *Phytopathology* 87:S90-91.

Sinisterra, X. H., J. E. Polston, A. M. Abouzid, E. Hiebert (1999) "Tobacco Plants Transformed with a Modified Coat Protein of Tomato Mottle Begomovirus Show Resistance to Virus Infection" *Phytopathology* 89(8):701-706.

Stout, J. T., H. T. Lui, J. E. Polston, R. L. Gilbertson, M. K. Nakhla, S. F. Hanson, D. P. Maxwell (1997) "Engineered rep gene-mediated resistance to tomato mottle geminivirus in tomato" *Phytopathology* 87:S94.

Williams, L., T. J. Dennehy, J. C. Palumbo (1996) "Development of a resistance management program for imidacloprid" Cotton Insect Research and Control Conference, 1996 Beltwide Cotton Conferences pp. 752-755.

We claim:

1. A transgenic plant or plant tissue having increased resistance to infection by a geminivirus plant virus, wherein said plant or plant tissue comprises a polynucleotide that comprises a nucleotide sequence that encodes a non-mutated Rep protein of a tomato mottle geminivirus, wherein said polynucleotide comprises the sequence shown in SEQ ID NO: 1.

2. A transgenic plant or plant tissue having increased resistance to infection by a geminivirus plant virus, wherein said plant or plant tissue comprises a polynucleotide that comprises a nucleotide sequence that encodes a non-mutated Rep protein of a tomato mottle geminivirus, wherein said non-mutated Rep protein has the amino acid sequence shown in SEQ ID NO: 2.

3. The transgenic plant or plant tissue according to claim 1, wherein said plant or plant tissue is tomato or tobacco.

4. The transgenic plant or plant tissue according to claim 1, wherein said geminivirus plant virus is a tomato mottle geminivirus.

5. The transgenic plant or plant tissue according to claim 1, wherein said plant tissue is a plant seed.

6. The transgenic plant or plant tissue according to claim 1, wherein said transgenic plant or plant tissue is a hybrid made by crossing a transgenic plant comprising a polynucleotide that encodes a non-mutated Rep protein of a tomato mottle geminivirus with a plant that does not comprise a polynucleotide that encodes a non-mutated Rep protein of a tomato mottle geminivirus.

7. The transgenic plant or plant tissue according to claim 1, wherein said transgenic plant or plant tissue is a hybrid made by crossing a first transgenic plant comprising a polynucleotide that comprises a nucleotide sequence that encodes a non-mutated geminivirus Rep protein of a tomato mottle geminivirus with a second transgenic plant comprising a polynucleotide that comprises a nucleotide sequence that encodes a non-mutated geminivirus Rep protein of a tomato mottle geminivirus.

8. The transgenic plant or plant tissue according to claim 7, wherein said second transgenic plant is derived from a transformation event distinct from the transformation event from which said first transgenic plant is derived.

9. A cell, or progeny thereof, transformed with a polynucleotide that comprises a nucleotide sequence that encodes a non-mutated Rep protein of a tomato mottle geminivirus, wherein said polynucleotide comprises the sequence shown in SEQ ID NO: 1.

10. A cell, or progeny thereof, transformed with a polynucleotide that comprises a nucleotide sequence that encodes a non-mutated Rep protein of a tomato mottle geminivirus, wherein said non-mutated Rep protein has the amino acid sequence shown in SEQ ID NO: 2.

11. The transgenic plant or plant tissue according to claim 2, wherein said plant or plant tissue is tomato or tobacco.

12. The transgenic plant or plant tissue according to claim 2, wherein said geminivirus plant virus is a tomato mottle geminivirus.

13. The transgenic plant or plant tissue according to claim 2, wherein said plant tissue is a plant seed.

14. The transgenic plant or plant tissue according to claim 2, wherein said transgenic plant or plant tissue is a hybrid made by crossing a transgenic plant comprising a polynucleotide that encodes a non-mutated Rep protein of a tomato mottle geminivirus with a plant that does not comprise a polynucleotide that encodes a non-mutated Rep protein of a tomato mottle geminivirus.

15. The transgenic plant or plant tissue according to claim 2, wherein said transgenic plant or plant tissue is a hybrid made by crossing a first transgenic plant comprising a polynucleotide that comprises a nucleotide sequence that encodes a non-mutated geminivirus Rep protein of a tomato mottle geminivirus with a second transgenic plant comprising a potynucleotide that comprises a nucleotide sequence that encodes a non-mutated geminivirus Rep protein of a tomato mottle geminivirus.

16. The transgenic plant or plant tissue according to claim 15, wherein said second transgenic plant is derived from a transformation event distinct from the transformation event from which said first transgenic plant is derived.

* * * * *

UNITED STATES PATENT AND TRADEMARK OFFICE
CERTIFICATE OF CORRECTION

PATENT NO. : 7,294,758 B2 Page 1 of 1
APPLICATION NO. : 11/134994
DATED : November 13, 2007
INVENTOR(S) : Jane E. Polston et al.

It is certified that error appears in the above-identified patent and that said Letters Patent is hereby corrected as shown below:

<u>Column 16</u>:
Line 9 "a potynucleotide" should read -- a polynucleotide --.

Signed and Sealed this

Thirty-first Day of March, 2009

JOHN DOLL
*Acting Director of the United States Patent and Trademark Office*